United States Patent
Camuso-Gianella et al.

(10) Patent No.: US 11,387,002 B2
(45) Date of Patent: Jul. 12, 2022

(54) AUTOMATED CANCER REGISTRY RECORD GENERATION

(71) Applicant: Elekta, Inc., Atlanta, GA (US)

(72) Inventors: Heidi Jo Camuso-Gianella, San Jose, CA (US); Sanjay Agrawal, St. Louis, MO (US)

(73) Assignee: Elekta, Inc., Atlanta, GA (US)

(*) Notice: Subject to any disclaimer, the term of this patent is extended or adjusted under 35 U.S.C. 154(b) by 188 days.

(21) Appl. No.: 16/354,090

(22) Filed: Mar. 14, 2019

(65) Prior Publication Data
US 2020/0294678 A1 Sep. 17, 2020

(51) Int. Cl.
| | | |
|---|---|---|
| *G16H 50/70* | (2018.01) | |
| *G16H 50/50* | (2018.01) | |
| *G16H 50/30* | (2018.01) | |
| *G16H 50/20* | (2018.01) | |
| *G16H 10/60* | (2018.01) | |
| *G16B 50/30* | (2019.01) | |
| *G16B 50/20* | (2019.01) | |

(52) U.S. Cl.
CPC .......... *G16H 50/70* (2018.01); *G16B 50/20* (2019.02); *G16B 50/30* (2019.02); *G16H 10/60* (2018.01); *G16H 50/50* (2018.01)

(58) Field of Classification Search
CPC ........ G16H 50/70; G16H 10/60; G16H 50/50; G16H 50/20; G16H 70/60; G16B 50/20; G16B 50/30
USPC ........................................................ 705/2
See application file for complete search history.

(56) References Cited

U.S. PATENT DOCUMENTS

2008/0275732 A1* 11/2008 Falchuk .............. G06Q 10/00
                                                        705/3
2012/0304054 A1* 11/2012 Orf .................... G16H 15/00
                                                        715/255
(Continued)

FOREIGN PATENT DOCUMENTS

WO    WO-2017160735 A1 *  9/2017 .......... G06F 16/256
WO       2020185899          9/2020

OTHER PUBLICATIONS

Meredith, Ineke et al.; Cancer in Pacific people in New Zealand; Cancer Causes & Control 23.7: 1173-84. Springer Nature B.V. (Jul. 2012) (Year: 2012).*

(Continued)

*Primary Examiner* — Hiep V Nguyen
(74) *Attorney, Agent, or Firm* — Schwegman Lundberg & Woessner, P.A.

(57) ABSTRACT

Techniques for generating cancer registry records are provided. The techniques include obtaining a plurality of rules that define cancer registry record generation as a function of patient health records; obtaining one or more electronic health records associated with a patient that include cancer related treatment information; processing the cancer related treatment information in the one or more electronic health records to generate a cancer registry record for the patient that represents a portion of the cancer related treatment information; determining that the cancer registry record includes insufficient cancer related treatment information; and updating the cancer registry record to address the insufficient cancer related treatment information by evaluating the cancer related treatment information against the plurality of rules.

20 Claims, 7 Drawing Sheets

(56) References Cited

U.S. PATENT DOCUMENTS

| | | | | |
|---|---|---|---|---|
| 2014/0330586 A1* | 11/2014 | Riskin | ................... | G16H 15/00 |
| | | | | 705/3 |
| 2015/0347699 A1 | 12/2015 | Vidwans et al. | | |
| 2015/0363553 A1* | 12/2015 | Rustgi | ................... | G06Q 10/06 |
| | | | | 705/3 |
| 2017/0235894 A1* | 8/2017 | Cox | ........................ | G06N 5/04 |
| | | | | 705/2 |

OTHER PUBLICATIONS

"International Application Serial No. PCT US2020 022106, International Search Report dated May 19, 2020", 4 pgs.
"International Application Serial No. PCT US2020 022106, Written Opinion dated May 19, 2020", 7 pgs.
"International Application Serial No. PCT US2020 022106, International Preliminary Report on Patentability dated Sep. 23, 2021", 9 pgs.

* cited by examiner

AUTOMATED CANCER REGISTRY RECORD GENERATION

TECHNICAL FIELD

Embodiments of the present disclosure relate generally to methods and systems for use of electronic patient data repositories, such as cancer registries, to manage patient treatment.

BACKGROUND

Electronic data repositories, such as registries established for trauma, transplant, and cancer patients, can be used to collect and store useful information for particular and potentially large populations over potentially long periods of time. For example, the Surveillance, Epidemiology, and End Results (SEER) Program, supported by the US National Cancer Institute (NCI), collects data for particular geographic areas and particular types of cancer, covering over 25% of the US population, with data for some locations going back to 1973. Such repositories can provide valuable data in quantities sufficient for meaningful analysis. Data is entered into such registries through a manual process that is subject to various regulatory rules, which takes a great deal of time and effort, which introduces long delays and inefficiencies in the data that is gathered. Also, it is difficult and tedious to ensure that all the rules are followed, which creates inaccuracies in the data that is ultimately entered.

OVERVIEW

The present disclosure includes procedures to generate cancer registry records.

In some embodiments, the techniques include a computer-implemented method, and a system comprising at least one processor and a storage medium comprising instructions to cause the processor to perform operations for obtaining a plurality of rules that define cancer registry record generation as a function of patient health records; obtaining one or more electronic health records associated with a patient that include cancer related treatment information; processing the cancer related treatment information in the one or more electronic health records to generate a cancer registry record for the patient that represents a portion of the cancer related treatment information; determining that the cancer registry record includes insufficient cancer related treatment information; and updating the cancer registry record to address the insufficient cancer related treatment information by evaluating the cancer related treatment information against the plurality of rules.

In some implementations, determining that the cancer registry record includes insufficient cancer related treatment information includes automatically determining that the cancer registry record includes missing or incomplete information. In some implementations, the cancer registry record is stored in a government-regulated registry.

In some implementations, the cancer related treatment information is processed by performing natural language processing to generate data representing the cancer related treatment information; identifying one or more cancer registry codes, based on the plurality of rules, that are associated with the generated data; and populating one or more fields in the cancer registry record based on the identified one or more cancer registry codes.

In some implementations, the one or more electronic health records are in a first format and the cancer registry record is in a second format.

In some implementations, the portion of the cancer related treatment information is determined to correspond to a cancer related treatment or diagnosis in response to processing the cancer related treatment information; the cancer related treatment or diagnosis is compared with a threshold representing a frequency of the cancer related treatment or diagnosis; and a notification is generated for a user to review the cancer registry record in response to determining that the cancer related treatment or diagnosis exceeds the threshold.

In some implementations, a determination is made, based on at least one of the rules, that data in a first field in the cancer registry record is inconsistent with data in a second field in the cancer registry record; additional cancer related treatment information is accessed from the one or more electronic health records to verify that the data in at least one of the first or second fields is correct; and the data in at least one of the first or second fields is updated based on the additional cancer related treatment information. In some implementations, the data in the first field indicates that the patient is a female and the data in the second field indicates a diagnosis of prostate cancer, and accessing the additional cancer related treatment information is performed by: retrieving at least one of medical imaging information or blood sample information from the one or more electronic health records; determining that the medical imaging information or the blood sample information corresponds to a male patient; and adjusting the data in the first field to indicate that the patient is a male or flagging the data for review.

In some implementations, a determination is made that a first type of data from the cancer related treatment information corresponds to a first code of a field in the cancer registry record; a determination is made that a second type of data from the cancer related treatment information corresponds to a second code of the field in the cancer registry record; the second type of data is prioritized over the first type of data based on the rules; and the field in the cancer registry record is populated with the second code instead of the first code based on the prioritizing. In some implementations, the first type of data represents results of a biopsy and the second type of data represents results from medical imaging.

In some implementations, a collection of cancer registry records, associated with a plurality of cancer patients, that are similar to the generated cancer registry record is identified; a treatment protocol indicated in the collection of cancer registry records is identified; and a recommended treatment protocol for treating the patient is produced based on the identified treatment protocol.

In some implementations, the one or more electronic health records are retrieved from a first database that manages cancer patients of a first hospital; one or more additional electronic health records are obtained from a second database that manages cancer patients of a second hospital; and the cancer registry record is stored among a plurality of cancer registry records in an inter-hospital registry that contains data about a population of cancer patients.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
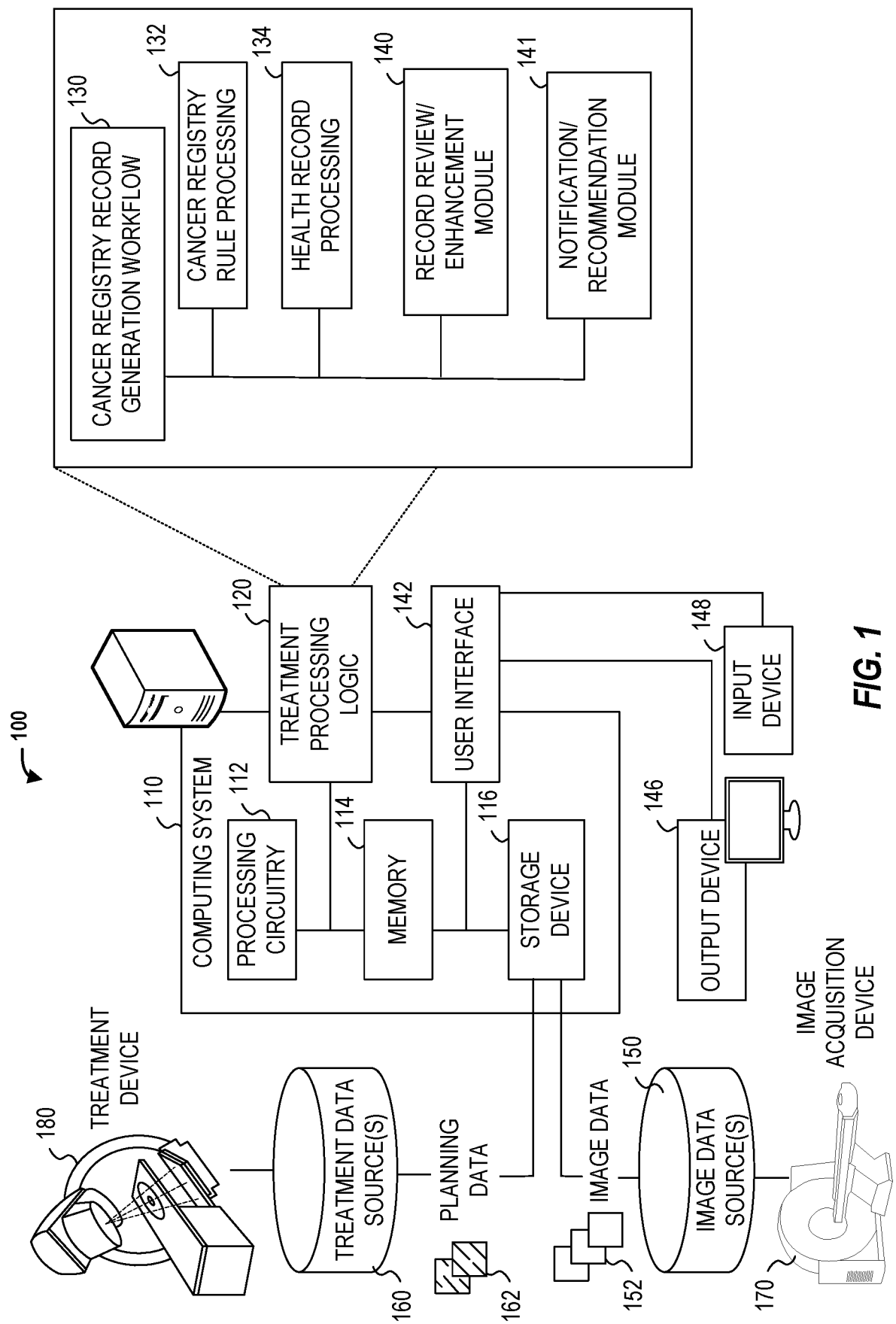
FIG. 1 illustrates an example radiotherapy system adapted for performing treatment plan generation processing according to some examples.

The present disclosure includes various techniques for generating cancer registry records. Specifically, the disclosed techniques obtain a plurality of rules that define cancer registry record generation as a function of patient health records and obtain one or more electronic health records associated with a patient that include cancer related treatment information. The cancer related treatment information in the one or more electronic health records is processed to generate a cancer registry record for the patient that represents a portion of the cancer related treatment information. The disclosed techniques determine that the cancer registry record includes insufficient cancer related treatment information and automatically update the cancer registry record to address the insufficient cancer related treatment information by evaluating the cancer related treatment information against the plurality of rules.

Typically, medical information can be contributed to data repositories by people who are trained and/or certified, and who gather, review, and input what they believe to be accurate information according to established standards. For example, cancer registrars input data to cancer registries as required by the North American Association of Central Cancer Registries' (NAACCR) Data Standards. Such data repositories are used to describe the incidence or prevalence of certain events—e.g., births, violent crimes, obesity, accidental deaths, and disease—in a particular population over a certain period of time. With certain privacy controls in place, electronic data repositories can be shared among programs and institutions and even made public. The SEER data, for example, are made available to researchers and the public, who have used the information to search for cancer trends, report cancer statistics by geographic region, and identify cancer risk factors. Such studies may be used to focus remedial efforts, such as education or outreach, in particular areas or on persons deemed to be at risk.

In many cases, the trained data entry personnel utilize NCI-provided reporting guidelines for completing cancer registry forms and various resources that assist clinicians with completing cancer registry forms. When a record has data that is properly entered, verified as being correct, and/or otherwise validated, the information contained therein is structured and uploaded to the cancer registry. While such a record creation process works well over time, the process of creating such records is very time-consuming and subject to some variation among clinicians. Specifically, the time needed to create a validated registry record is often long, and for many cancer registries, data for a patient is first entered many months or even years after the patient is diagnosed with cancer. The entry is done one field at a time, based upon the registrar's assessments of multiple potentially contradictory sources of information, in a process that is slow, tedious, repetitive, and time-consuming. Registrars may have multiple cases waiting in a queue that are in various states of completeness due to difficulties in validating or obtaining the necessary data. Not surprisingly, additional data for the patient may be provided infrequently, for example, upon cure, five years thereafter, and upon death. The utility of registry records is often limited by the difficulty in providing validated registry records. Also, because of the long delays in creating and validating such records in the repositories, often the studies that utilize the records generate results that are based on stale data and fail to reflect the most up-to-date conditions of the population.

In an effort to address such inefficiencies and poor data analysis, the disclosed techniques automatically (without receiving user input) process patient medical information and automatically (without receiving user input) utilize rules to create medical records that are accurate. The disclosed techniques curate electronic records for cancer patients that are reliable and accurate, and/or the disclosed techniques augment registry records with additional sources of medical information that can be readily accessed to provide just-in-time insights on cancer treatment methods, trends, etc. This ensures that the data reflected in the repositories of the states and/or hospitals is up to date with the latest medical information available about a given population.

Specifically, in some embodiments the present human and knowledge resources used to create and update registry records are substantially obviated and augmented, respectively. A clinician's time spent checking and correcting a rejected registry record is reduced if not eliminated. Additionally, the disclosed embodiments address the need for providing validated records on a more timely basis so that the structured information contained therein can be of greater value and utility to stakeholders such as medical professionals, researchers, and biopharma and medical device companies.

In some embodiments, content of a validated registry record is enhanced. Specifically, resources available from a data repository of a hospital are used to supplement information found in a validated registry record. For example, in one embodiment, a registry record is supplemented by adding information that describes a specific modality used to treat a patient, and optionally parameters such as dosage, duration of treatment, and indications unique to treatment by that modality, which were recorded or observed during the course of treatment. In some embodiments, an inter-hospital registry is created using validated registry records and/or enhanced registry records. The inter-hospital registry may be used to augment a physician's available resources when the physician is selecting or modifying a treatment protocol for her patient. For example, the inter-hospital registry can provide benchmarking data for treatments that used a specific type of modality for a given condition and patient demographic. Given the diversity and number of enhanced registry records that can accumulate in an inter-hospital registry, its beneficiaries can include physicians, researchers, and drug and medical-device companies looking for clinical trial candidates, for example. Registry records or enhanced registry records (provided either through a hospital's registry or via the inter-hospital registry) are used with other patient data to augment a physician's decision making when she is planning a treatment protocol for a patient.

In some embodiments, natural language processing is performed to process the cancer related treatment information received from one or more hospitals for a given patient. The data resulting from the natural language processing is analyzed according to specified rules to identify one or more cancer registry codes associated with the data. A cancer registry template is retrieved and fields of the cancer registry template are automatically (without receiving user input) populated using the identified cancer registry codes. After the record is automatically (without receiving user input) generated (which may be in a different format than the cancer related treatment information that is received), the record is processed to determine whether sufficient cancer related information is included. This can be done by determining whether the record includes missing or incomplete information.

In some implementations, the specified rules are utilized to determine whether data in a first field in the cancer registry record is inconsistent with data in a second field in the cancer registry record. For example, the data in the first field may indicate that the patient is a female, and the data in the second field may indicate a diagnosis of prostate cancer, which is inconsistent with female patients. In such circumstances, additional cancer related treatment information is accessed from one or more electronic health records of the patient to verify that the data in at least one of the first or second fields is correct. For example, at least one of medical imaging information or blood sample information may be retrieved from the one or more electronic health records, and a determination can be made that the medical imaging information or blood sample information corresponds to a male patient. The data in at least one of the first or second fields is then updated based on the additional cancer related treatment information, or a notification can be provided in a graphical user interface to inform a clinician about the inconsistency for clinician review.

In some embodiments, the disclosed techniques determine whether a portion of the cancer related treatment information corresponds to a cancer related treatment or diagnosis. The cancer related treatment or diagnosis is compared with a threshold representing a frequency of the cancer related treatment or diagnosis across a larger population. If the treatment or diagnosis exceeds the threshold, a notification is generated and displayed to a clinician or user in a graphical user interface indicating the cancer related treatment or diagnosis. The clinician can then review the automatically generated record to verify the accuracy of the cancer related treatment or diagnosis.

In some embodiments, a collection of cancer registry records, associated with a plurality of cancer patients, that are similar to the generated cancer registry record is obtained. A treatment protocol indicated in the collection of cancer registry records is identified and used to produce a recommended treatment protocol for treating the patient. Such a recommendation can be provided to a clinician in a graphical user interface for the clinician to review and accept.

FIG. 1 illustrates an exemplary radiotherapy system 100 adapted for performing treatment plan generation processing using one or more of the approaches discussed herein. These radiotherapy plan processing operations are performed to enable the radiotherapy system 100 to provide radiation therapy to a patient based on specific aspects of captured medical imaging data and therapy dose calculations. The radiotherapy system 100 may automatically generate and validate cancer registry records. For example, the radiotherapy system 100 may obtain cancer related treatment information for a given patient, and perform natural language processing to obtain cancer related data which is analyzed together with specified rules to identify one or more cancer registry codes associated with the data. A cancer registry template may be retrieved, and fields of the record may be automatically populated using the identified cancer registry codes.

The radiotherapy system 100 includes a radiotherapy processing computing system 110 which hosts treatment processing logic 120. The radiotherapy processing computing system 110 may be connected to a network (not shown), and such a network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and one or more treatment data sources 160. As an example, the radiotherapy processing computing system 110 can be configured to receive cancer related treatment information 162, such as dose information or a Magnetic Resonance (MR) image, of a subject and automatically generate a cancer registry record by applying rules to obtain codes that represent the cancer related treatment information, such as by executing instructions or data from the treatment processing logic 120, as part of operations to generate the registry record to be used by the treatment device 180 and/or for output on an output device 146.

The radiotherapy processing computing system 110 may include processing circuitry 112, memory 114, a storage device 116, and other hardware- and software-operable features such as a user interface 142, a communication interface (not shown), and the like. The storage device 116 may store transitory or non-transitory computer-executable instructions, such as an operating system, radiation therapy treatment plans (e.g., training cone beam computer tomography (CBCT) images, real computer tomography (CT) images, paring information that associates the training and real CT images, adapted or modified CBCT images, and the like), software programs (e.g., image processing software, image or anatomical visualization software, AI implementations and algorithms such as provided by DL models, machine learning (ML) models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a system on a chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, a microprocessor from the Turion™, Athlon™, Sempron™, Opteron™, FX™, or Phenom™ family manufactured by AMD™, or any of various processors manufactured by Sun Microsystems. The processing circuitry 112 may also include graphical processing units such as a GPU from the GeForce®, Quadro®, or Tesla® family manufactured by Nvidia™, the GMA or Iris™ family manufactured by Intel™, or the Radeon™ family manufactured by AMD™. The processing circuitry 112 may also include accelerated processing units such as units from the Xeon Phi™ family manufactured by Intel™. The disclosed embodiments are not limited to any type of processor(s) but may be embodied on any processor configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor, for example, a processor having a multi-core design or a plurality of processors each having a multi-core design. The processing circuitry 112 can execute sequences of transitory or non-transitory computer program instructions, stored in the memory 114, and accessed from the storage device 116, to perform various operations, processes, and methods that will be explained in greater detail below. It should be understood that any component in the radiotherapy system 100 may be implemented separately and operate as an independent device and may be coupled to any other component in the radiotherapy system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory), other types of random access memories, a cache, a register, a compact disc read-only memory (CD-ROM), a digital versatile disc (DVD) or other optical storage device, a cassette tape, another magnetic storage device, or any other non-transitory medium that may be used to store information including images, data, or transitory or non-transitory computer-executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, dose histograms, dose measurements, AI model data (e.g., weights and parameters), labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, a USB flash drive, an SD card, a memory stick, or any other suitable medium; such software programs may also be communicated or received over a network.

The memory 114 may be distributed across multiple hospitals or state registries. The memory 114 may be used to store the cancer related treatment information and cancer registry records discussed with respect to FIGS. 2-7. Cancer related treatment information includes analog, digital, audio, visual, structured, or unstructured data—associated with a diagnosed or undiagnosed patient—that is maintained at one or more health care facilities, such as a hospital. The cancer related treatment information may include one or more of an existing or planned treatment protocol, an enhanced registry record, a recommended protocol, a registry record provided to a state registry, an insurance provider, payment records, a diagnosed condition, a pathological record, an immunization registry record, a trauma registry record, and epidemiologic or radiologic data. A registry record includes structured data about a patient that is composed of fields that include one or more items of information or codes representing cancer related information. A registry record for a patient may be defined by a state or other authority, for example, through a menu-driven software application that provides a user with a template for entering data into different fields of the record.

Although they are not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, Thunderbolt, and the like), a wireless network adaptor (e.g., such as an IEEE 802.11/Wi-Fi adapter), a telecommunication adapter (e.g., to communicate with 3G, 4G/LTE, and 5G networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server environment, a wide area network (WAN), and the like. For example, the network may be a LAN or a WAN that may include other systems (including additional image processing computing systems or image-based components associated with medical imaging or radiotherapy operations).

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from image data 152 and/or cancer related treatment information to be received or obtained in the memory 114 and processed using the treatment processing logic 120. In further examples, the processing circuitry 112 may utilize software programs (e.g., image processing software) along with the image data 152 and other patient data to automatically generate cancer registry records.

In an example, the image data 152 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), computed tomography (CT) images (e.g., 2D CT, 2D Cone beam CT, 3D CT, 3D CBCT, 4D CT, 4D CBCT), ultrasound images (e.g., 2D ultrasound, 3D ultrasound, 4D ultrasound), positron emission tomography (PET) images, X-ray images, fluoroscopic images, radiotherapy portal images, single-photon emission computed tomography (SPECT) images, computer-generated synthetic images (e.g., pseudo-CT images), and the like. Further, the image data 152 may also include or be associated with medical image processing data, for instance, training images, ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a picture archiving and communication system (PACS), a vendor neutral archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an integrated linear accelerator and MRI imaging device, a CBCT imaging device, or other medical imaging devices for obtaining medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The radiotherapy processing computing system 110 may communicate with an external database through a network to send and receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on- and off-time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located in either a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from the output device 146 or an input device 148 to connect to the user interface 142, which may be a hardware keyboard, a keypad, or a touch screen through which a user may input information into the radiotherapy system 100.

Figure 7:
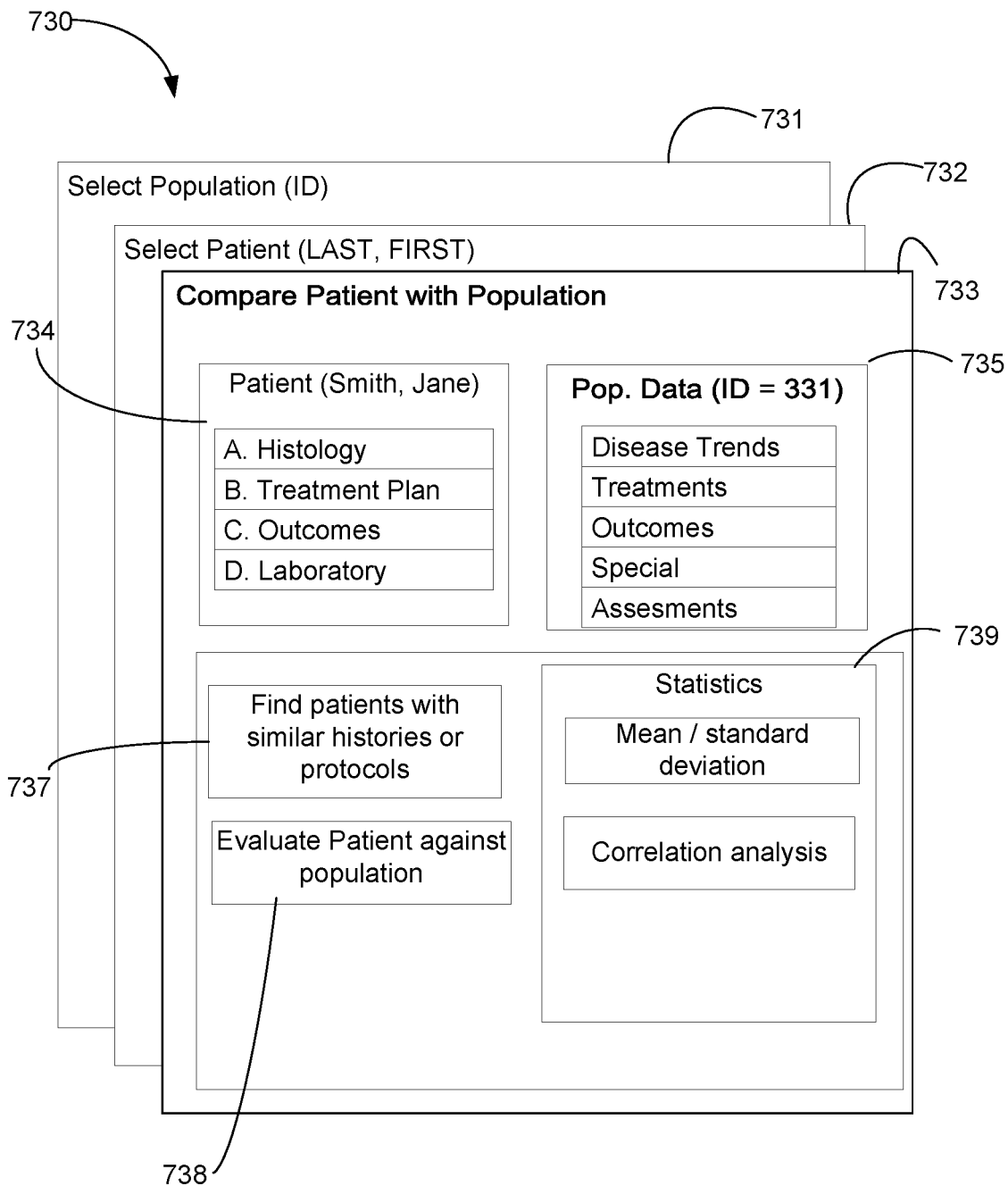
FIG. 7 illustrates an example user interface of the cancer registry record-generation workflow according to some examples of the disclosure.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may output a graphical user interface as depicted in FIG. 7. The output device 146 may include one or more display screens that display medical images, interface information, treatment planning parameters (e.g., contours, dosages, beam angles, labels, maps, etc.), treatment plans, a target, information related to localizing a target and/or tracking a target, or any related information to the user. The input device 148 connected to the user interface 142 may be a keyboard, a keypad, a touch screen, or any type of device that a user may use to input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms)

or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components may be implemented as a virtual machine or within a cloud-based virtualization environment.

The treatment processing logic 120 or other software programs may cause the radiotherapy processing computing system 110 to communicate with the image data sources 150 to read images into the memory 114 and the storage device 116 from the image data sources 150, or to store images or associated data from the memory 114 or the storage device 116 to the image data sources 150. For example, the image data source 150 may be configured to store and provide a plurality of images (e.g., 3D MRI, 4D MRI, 2D MRI slice images, CT images, 2D fluoroscopy images, X-ray images, raw data from MR scans or CT scans, Digital Imaging and Communications in Medicine (DICOM) metadata, etc.) that the image data source 150 hosts, from image sets in the image data 152 obtained from one or more patients via the image acquisition device 170 in model training or generation use cases. The radiotherapy processing computing system 110 thus may obtain and/or receive the image data 152 (e.g., 2D MRI slice images, CT images, 2D fluoroscopy images, X-ray images, 3D MRI images, 4D MRI images, etc.) from the image data source 150, the image acquisition device 170, the treatment device 180 (e.g., an MRI-Linac), or other information systems, in connection with performing radiation treatment or diagnostic operations.

The image acquisition device 170 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT, or MRI volume. Such 2D slices can be acquired by the image acquisition device 170 in "near-real time" while a patient is undergoing radiation therapy treatment, for example, when using the treatment device 180 (with "near-real time" meaning acquiring the data in at least milliseconds or less).

The treatment processing logic 120 in the radiotherapy processing computing system 110 is depicted as implementing a cancer registry record-generation workflow 130. The cancer registry record-generation workflow 130 may include cancer registry rule processing 132, health record processing 134, a record review/enhancement module 140, and a notification/recommendation module 141. In some embodiments, the cancer registry record-generation workflow 130 receives an instruction, such as via a graphical user interface of the input device 148, to generate a cancer registry record for a given patient. The cancer registry record-generation workflow 130 may receive a patient identifier via the graphical user interface. In response, the cancer registry record-generation workflow 130 may obtain cancer related treatment information for the patient from one or more hospitals that may be stored in the storage device 116. The cancer registry record generation workflow 130 processes the cancer related treatment information using one or more disclosed techniques to automatically generate a cancer registry record and/or enhance an already available record for the patient. Once the cancer registry record has been generated or enhanced, the cancer registry record-generation workflow 130 stores the automatically generated or enhanced record in a state registry (e.g., in the storage device 116) and/or makes the record available to one or more hospitals.

In some embodiments, the cancer registry record-generation workflow 130 instructs the health record processing 134 to obtain cancer related treatment information for the identified patient. The health record processing 134 uses the unique patient identifier provided by the input device 148 to search one or more databases available from one or more hospitals and/or cancer registries for the cancer related treatment information. In some implementations, the cancer related treatment information includes a previously generated cancer registry record, tumor geometry information, images of the cancer region of the patient, oncology reports, dose information, radiotherapy treatment plans, diagnosis information, survival rate, and/or any other suitable electronically available health information. In some implementations, the health record processing 134 performs natural language processing to convert any handwritten notes to computer-readable information in the cancer related treatment information. The health record processing 134 identifies key terms in the processed handwritten notes that indicate patient gender, dose information, treatment plans, diagnosis, and so forth.

The health record processing 134 communicates with the cancer registry rule processing 132 to cross-reference any combination of information and/or key terms generated or retrieved from the cancer related treatment information for the patient with a set of rules obtained by the cancer registry rule processing 132. Specifically, the cancer registry rule processing 132 may detect a condition associated with the patient, either automatically or based on information provided via the graphical user interface by a physician. The cancer registry rule processing 132 accesses one or more publicly available regulatory cancer registry databases that contain rules that associate various key terms, conditions, combinations of conditions, cancer related treatment information, and geometrical information of a tumor with one or more corresponding cancer registry codes. The health record processing 134 matches the key terms and any combinations of the cancer related treatment information with the codes in the rules. The health record processing 134 retrieves the codes and the fields of a cancer registry record associated with the codes. The health record processing 134 communicates the retrieved codes and fields to the record review/enhancement module 140.

The record review/enhancement module 140 determines whether a cancer registry record has previously been created for the patient associated with the unique identifier. In response to determining that a record has not been previously created, the record review/enhancement module 140 retrieves various biographical information (e.g., gender, residence, name, age, etc.) of the patient from the health record processing 134 and/or supplied by the physician via the input device 148. The record review/enhancement module 140 obtains a template for a cancer registry record and automatically populates the biographical information in corresponding biographical fields of the template using the retrieved biographical information of the patient. The record review/enhancement module 140 also identifies one or more fields in the template that correspond to the fields associated with the codes identified by the health record processing 134. The record review/enhancement module 140 populates those fields with the codes received from the health record processing 134.

In some implementations, a record may have previously been created for the patient. In such cases, the record review/enhancement module 140 determines a last modified date of the previously created record. The record review/enhancement module 140 determines whether the cancer related treatment information used by the health record processing 134 to identify codes from the cancer registry rule processing 132 is associated with a later date than the last modified date of the previously created record. For example, the record may have been previously generated based on a first set of MRI images and a radiotherapy dose delivered on a particular date, such as Mar. 1, 2018. The record review/enhancement module 140 may determine that a second set of MRI images were obtained and a radiotherapy dose was delivered on Dec. 1, 2018. In response, the record review/enhancement module 140 determines that the record contains insufficient cancer related treatment information and may instruct the health record processing 134 to generate a set of codes based on the cancer related treatment information that was obtained on a date that follows the last modified date of the previously created record. The record review/enhancement module 140 may then obtain the codes from the health record processing 134 and store the codes in the corresponding fields of the record and/or update previously stored codes with new codes for the fields in the record.

In some embodiments, the record review/enhancement module 140 reviews the information in a given cancer registry record to detect inconsistencies. This may be done continuously by cycling through the various records stored in the cancer registry, periodically, such as once a month for every record, and/or in response to a specific user request identifying a given record or patient. The record review/enhancement module 140 may access a set of rules stored by the cancer registry rule processing 132 that indicate different types of errors or inconsistencies.

For example, the rules may indicate that a female patient cannot be diagnosed with prostate cancer. The rules may indicate that a male patient cannot be diagnosed with breast cancer. The rules may indicate that a certain amount of radiation or dose distribution for a given diagnosis in a certain region cannot exceed a specified amount. The rules may indicate that a geometric size of a tumor cannot exceed a geometric size of an organ and/or cannot be located in a particular region of the patient. The rules may be manually updated over time based on input from a physician received via a graphical user interface.

The record review/enhancement module 140 may compare the fields associated with the rules in a record with the parameters of the rules to detect inconsistencies. For example, the record review/enhancement module 140 may retrieve a gender specified in the record and the diagnosis specified in the record. The record review/enhancement module 140 may access a rule specifying a particular impossibility for a given gender (e.g., a female patient cannot be diagnosed with prostate cancer). The record review/enhancement module 140 may determine that the information in the record violates a condition of the rule (or corresponds to the impossibility indicated by the rule) by determining that the record has a field indicating a female gender and the diagnosis code in the diagnosis field indicates prostate cancer. As another example, the record review/enhancement module 140 may determine that the information in the record violates a condition of the rule (or corresponds to the impossibility indicated by the rule) by determining that the record has a field indicating a given geometry size of the tumor in the patient and another field identifying a type of the tumor and corresponding size which exceeds a maximum geometry size for the particular type of tumor specified in the rule.

In response to determining that the record violates the rule condition, the record review/enhancement module 140 instructs the health record processing 134 to obtain additional information about the patient. For example, the record review/enhancement module 140 may instruct the health record processing 134 to obtain blood information associated with the patient. The record review/enhancement module 140 may process the blood information to determine that the patient is a male. The record review/enhancement module 140 may determine that the gender indicated in the field of the record indicates female and may automatically update the gender to indicate that the patient is a male.

In some implementations, additional information that resolves the inconsistency may not be available to the health record processing 134. For example, blood information may not be available yet for the patient. In such circumstances, the record review/enhancement module 140 may communicate with the notification/recommendation module 141 to alert the physician or clinician about the inconsistency in the cancer registry record. The notification/recommendation module 141 may present a graphical user interface that visually distinguishes the fields that are detected to violate the rule condition or that are inconsistent. The notification/recommendation module 141 may receive input via the graphical user interface and the input device 148 from the physician that corrects the inconsistency, and the record may be updated and stored in the storage device 116.

In some embodiments, the record review/enhancement module 140 may automatically access population information for a given set or combination of fields in a cancer registry. For example, the record review/enhancement module 140 may select tumor type, tumor geometry, gender, age, diagnosis, and dose information fields as a combination of fields for which to search population information. The record review/enhancement module 140 may retrieve the patient information specified in the registry record for a particular patient in the selected fields and find similarly situated patients in the population. For example, the record review/enhancement module 140 may access a plurality of records from the entire or a subset of the population stored in the cancer registry and obtain the information stored in the selected fields. The record review/enhancement module 140 may filter all the records to those records of patients that are of the same gender and have the same tumor type, same tumor geometry, and same diagnosis as the particular patient. The record review/enhancement module 140 may generate an average or other statistical measure of the dose information contained in the filtered retrieved records to determine particular dose information.

The record review/enhancement module 140 may compare the particular dose information representative of the population with the same gender, same tumor type, same tumor geometry, and same diagnosis as the particular patient with the dose information stored in the field of the record for the particular patient. The record review/enhancement module 140 may determine whether the dose information stored in the field for the particular patient is within a threshold value or range (e.g., within 1-2 percent) of the particular dose information representative of the population. In response to determining that the dose information exceeds the threshold, the record review/enhancement module 140 instructs the notification/recommendation module 141 to generate a notification for display in a graphical user interface to a physician indicating that the dose exceeds the population dose. Alternatively, or in addition, if a dose is not stored in the field of the record for the patient, the record review/enhancement module 140 may enhance the record by inputting the particular dose information representing the population in the record for the patient. The record review/enhancement module 140 may instruct the notification/recommendation module 141 to generate a notification for display in a graphical user interface to a physician indicating the automatically generated recommendation for the dose.

Further details and examples of the treatment processing logic 120 automatically generating cancer registry records are provided in FIGS. 3-7.

Figure 2:
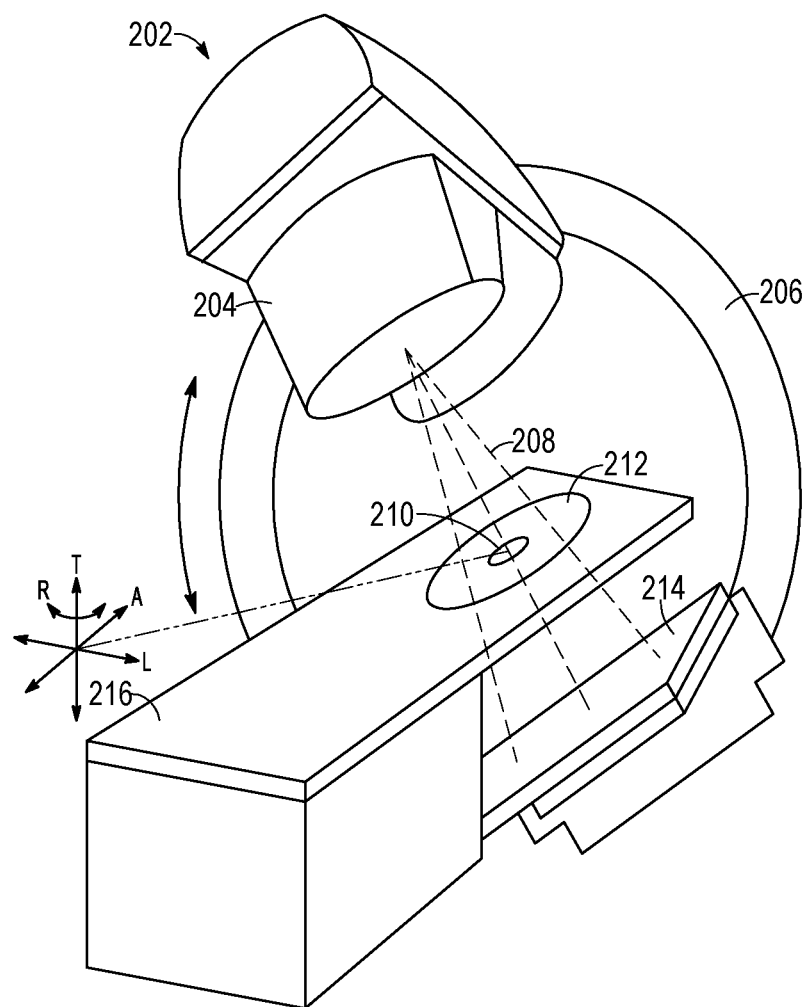
FIG. 2 illustrates an example image-guided radiotherapy device according to some examples of the disclosure.

FIG. 2 illustrates an exemplary image-guided radiotherapy device 202 that includes a radiation source, such as an X-ray source or a linear accelerator, a couch 216, an imaging detector 214, and a radiation therapy output 204. The image-guided radiotherapy device 202 may be configured to emit a radiation therapy beam 208 to provide therapy to a patient. The radiation therapy output 204 can include one or more attenuators or collimators, such as a multi-leaf collimator (MLC).

As an example, a patient can be positioned in a region 212, supported by the couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around the couch 216 when the couch 216 is inserted into the treatment area. In an example, the gantry 206 may be continuously rotatable around the couch 216 when the couch 216 is inserted into the treatment area. In another example, the gantry 206 may rotate to a predetermined position when the couch 216 is inserted into the treatment area. For example, the gantry 206 can be configured to rotate the radiation therapy output 204 around an axis ("A"). Both the couch 216 and the radiation therapy output 204 can be independently movable to other positions around the patient, such as movable in a transverse direction ("T"), movable in a lateral direction ("L"), or movable by rotation about one or more other axes, such as rotation about a transverse axis (indicated as "R"). A controller communicatively connected to one or more actuators (not shown) may control the couch 216 movements or rotations in order to properly position the patient in or out of the radiation therapy beam 208 according to a radiation therapy treatment plan. Both the couch 216 and the gantry 206 are movable independently from one another in multiple degrees of freedom, which allows the patient to be positioned such that the radiation therapy beam 208 can precisely target the tumor.

The coordinate system (including axes A, T, and L) shown in FIG. 2 can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

The gantry 206 may also have an attached imaging detector 214. The imaging detector 214 is preferably located opposite the radiation source (e.g., the radiation therapy output 204), and in an example, the imaging detector 214 can be located within a field of the radiation therapy beam 208. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation therapy beam 208, or the imaging detector 214 can be used for imaging the patient's anatomy, such as by portal imaging. The control circuitry of the image-guided radiotherapy device 202 may be integrated within the radiotherapy system 100 or remote from it.

In an illustrative example, one or more of the couch 216, the radiation therapy output 204, or the gantry 206 can be automatically positioned, and the radiation therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or radiation therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Figure 3:
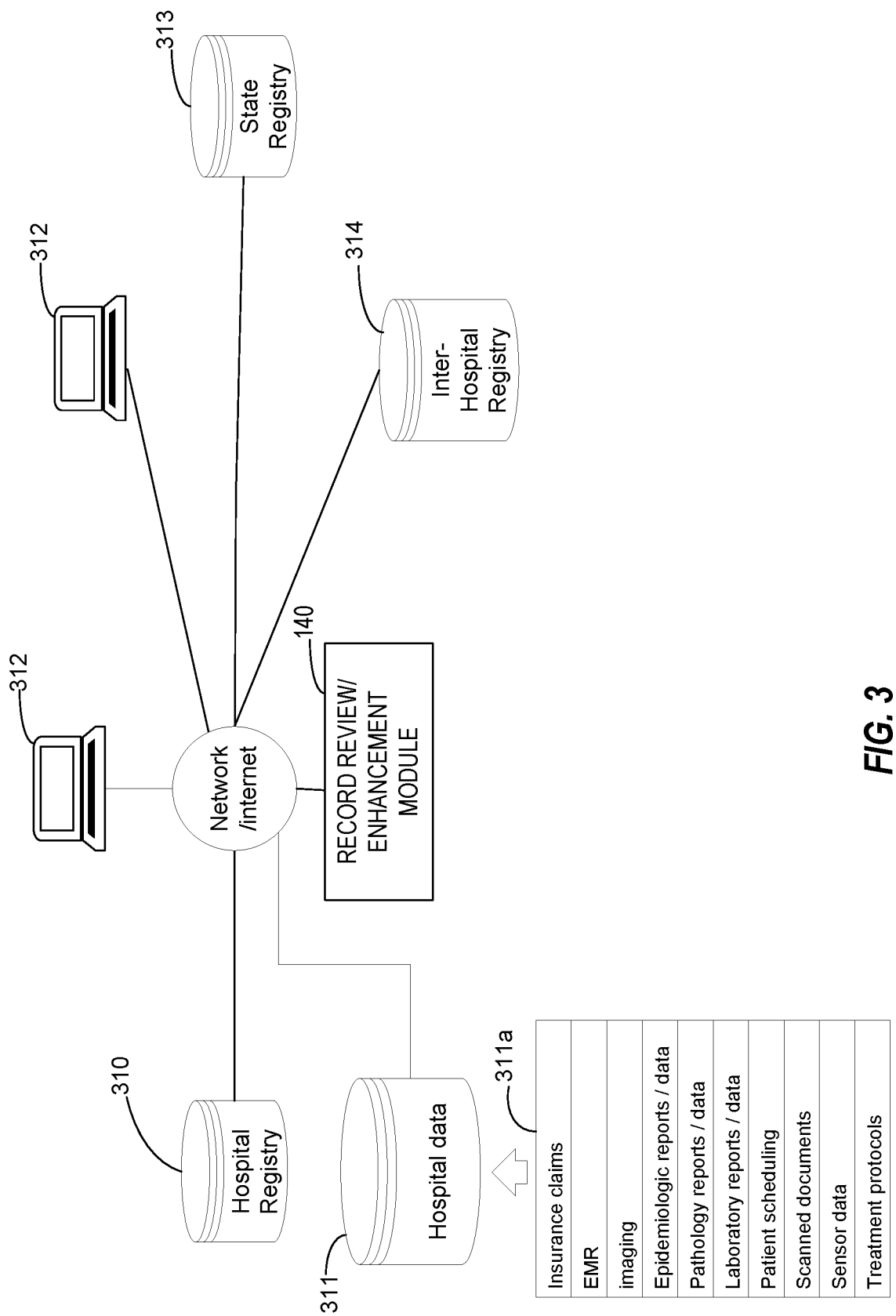
FIGS. 3-4 illustrate examples of a cancer registry record-generation workflow according to some examples of the disclosure.

FIG. 3 illustrates an example of the cancer registry record-generation workflow according to some examples of the disclosure. FIG. 3 shows a network that includes a hospital registry 310, a hospital data repository 311 for storing and managing hospital data, an inter-hospital registry 314, and one or more input and user interface devices 312. Users and/or applications running over the network may be communicatively connectable over the Internet to a state registry 313 and the inter-hospital registry 314. The network includes one or more computers including general-purpose processors for executing code, read and write functions, and network connectivity.

The hospital data repository 311 is a data repository that stores a variety of information relating to hospital functions such as accounting, employees, human resources, physicians, support staff, nurses, etc., and medical information about patients admitted or treated at a hospital or under the supervision of hospital staff. The categories of information 311a shown in FIG. 3 are only examples of information stored in the hospital data repository 311. The data in the hospital data repository 311 may be organized in a database format or a data lake format, and/or it may have a collection of flat or structured files organized under a file directory system according to the general subject matter, e.g., oncology or accounting. Data stored in the hospital data repository 311 is stored in a wide variety of data formats including structured and unstructured data formats, in different and sometimes incompatible file formats. The hospital data repository 311 stores cancer related treatment information for various patients of the hospital. In some embodiments, the memory 114 may store all or portions of the hospital data repository 311.

The hospital registry 310 is a data repository storing validated registry records for patients. Such records may include records that were automatically generated by the cancer registry record-generation workflow 130 based on cancer related patient information stored in the hospital data repository 311. The hospital registry 310 stores data from the registry records in a database format such that information contained in the fields of the records may be readily retrieved from a user- or machine-initiated search query of information contained in one or more registry records.

The state registry 313 is accessed over the Internet and represents a designated location for upload of a validated registry record for a patient for hospitals operating within the jurisdiction of the state. Registry records may be created from patient data contained in the hospital data repository 311. Registry validation application software (e.g., the record review/enhancement module 140) is used to create, populate, and validate a registry record. A registry record may be validated by the record review/enhancement module 140 before it is uploaded to the state registry 313. The record review/enhancement module 140 includes a template and menu-driven system for automatically or semi-automatically entering the patient data. The user interface and menu system is used by a registrar or other qualified person (using an input and user interface device 312) to enter data about a newly diagnosed or existing patient, such as demographics, the type of disease, the duration of treatment, and the progression of the disease since first diagnosed. When a record is completed and validated by the record review/enhancement module 140 it is uploaded to the state registry 313, and a copy is stored in the hospital registry 310.

Figure 4:
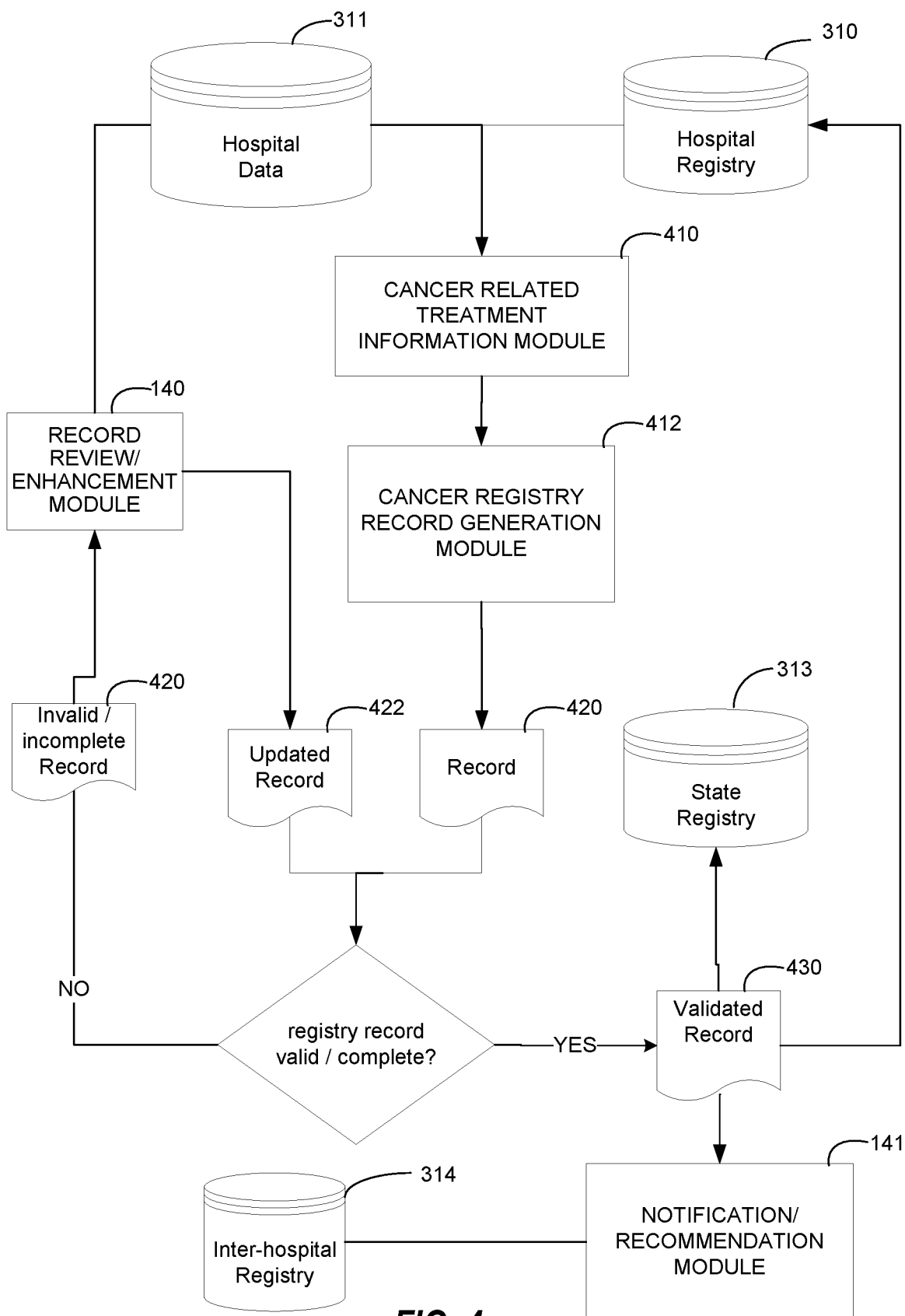

FIG. 4 illustrates an example of the cancer registry record-generation workflow according to some examples of the disclosure. The record review/enhancement module 140 of the cancer registry record-generation workflow 130 is called either when a patient has been recently diagnosed, for example, with cancer (as indicated by an International Classification of Diseases (ICD) code of 10) or when an updated registry record is needed for a previously diagnosed patient. In either case, the record review/enhancement module 140 is called to automatically prepare or update the patient's registry record by accessing available cancer related treatment information about the patient, e.g., in a spreadsheet or SQL database.

In some embodiments, a cancer related treatment information module 410 (which may implement the health record processing 134) obtains cancer related treatment information about a patient. This can be done by retrieving cancer related treatment information based on a unique patient identifier from databases of one or more hospitals. The obtained information is provided to a cancer registry record-generation module 412. The cancer related treatment information module 410 and cancer registry record-generation module 412 may be implemented as separate modules of the treatment processing logic 120 and/or as part of the record review/enhancement module 140. The cancer registry record-generation module 412 communicates with one or more state registries to obtain cancer registry rules associated with a given state. The cancer registry record-generation module 412 applies the retrieved rules to the cancer related treatment information received from the cancer related treatment information module 410 to identify one or more codes associated with each particular condition or set of conditions specified in the cancer related treatment information. The cancer registry record-generation module 412 populates a cancer registry template based on the codes by automatically entering the identified codes into the corresponding fields of the template. The cancer registry record-generation module 412 outputs a new cancer registry record 420. In an embodiment, the cancer registry record-generation module 412 obtains an old cancer registry record, identifies a set of cancer related treatment information that has been updated since generation of the old cancer registry record, and identifies codes and fields of the template corresponding only to the newly updated cancer related treatment information.

The record review/enhancement module 140 determines whether the record 420 is incomplete, contains invalid data, or contains data that is incompatible with other data entered in the record 420. In such cases, the record 420 is rejected as invalid. When the record 420 is rejected, the record review/enhancement module 140 addresses the problem automatically and, if possible, provides an updated record 422. The record review/enhancement module 140 may operate as a standalone program. The record review/enhancement module 140 analyzes the source of the error(s) that resulted in the record 420 rejection, finds a solution if possible, and produces the updated record 422. This updated record 422 is then input to the record review/enhancement module 140, which then evaluates it. If all errors have been corrected, the record review/enhancement module 140 may then validate the updated record 422 and upload it to the state registry 313.

In some embodiments, the record review/enhancement module 140 is configured to determine a value in one field (e.g., EMR code) that is valid, but inconsistent or in conflict with data entered in another part of the record (e.g., a patient received treatment one month after the patient died). In such cases, the record review/enhancement module 140 automatically retrieves additional information about the patient to resolve the inconsistency. If additional information is not available or does not address the inconsistency, the record review/enhancement module 140 flags the error and generates a notification for an operator to review the inconsistency using a graphical user interface.

In some embodiments, the record review/enhancement module 140 is configured to determine that the data location accessed by the record review/enhancement module 140 contains information for a field of the record from two sources that contradict each other. In such circumstances, the record review/enhancement module 140 obtains a priority assigned to each source and replaces or resolves the contradiction automatically by populating the field with the data from the source having the higher priority. Alternatively, or in addition, the record review/enhancement module 140 flags the error and generates a notification for an operator to review the contradiction using a graphical user interface. For example, the record review/enhancement module 140 may determine that the registry record includes a diagnostic date for a chest X-ray from pathology records that is January 1, which conflicts with the date entered for the same diagnostic in oncology (e.g., February 2). In such circumstances, the record review/enhancement module 140 automatically resolves this conflict by determining that the diagnostic in oncology is associated with a higher priority value than pathology records. Accordingly, the record review/enhancement module 140 updates the registry record to indicate the date for the chest X-ray to be February 2 rather than January 1.

In some implementations, using the registry field code(s) for the diagnostic date, the record review/enhancement module 140 accesses a subject-matter knowledge source to identify sources of information that might resolve the conflicting dates. The identified sources could include things like specific persons, jobs functions, or departments (e.g., oncology, pathology, radiology, etc.). Using the identified sources as a search guide, the record review/enhancement module 140 accesses a location knowledge source to identify areas in the hospital data repository 311 to search for information that might resolve the missing date, and collect data from identified areas. The record review/enhancement module 140 may analyze the collected data, including determining whether a first portion of the data or a second portion of the data is more reliable than the other, and based on that determination automatically updates the diagnostic date in the registry field for the updated record 422.

The identified sources may be either selected automatically, for example, by an algorithm or possible sources presented in a GUI, or selected by a user using the input and user interface device 312. In either case, the user may designate the areas or departments to be searched for clarifying information. In some implementations, the record review/enhancement module 140 may invoke a scoring system that gives more or less weight to data veracity depending on its source. The scoring system may include weights that attach to data retrieved from one source versus another source, where the weight is proportional to the reliability of the data source.

In some embodiments, the record review/enhancement module 140 enhances the data included in the records with additional information. For example, the record review/enhancement module 140 evaluates the fields in the generated record and compares the record to records of other patients. By identifying similarities between the records, the record review/enhancement module 140 can supplement the information included in a given record. For example, if a particular MR image of a given patient identifies a target region of a tumor having a particular geometry and size, the record review/enhancement module 140 may identify a threshold number of other patient records that indicate similar target regions of similar geometries and sizes that were previously successfully treated. The record review/enhancement module 140 may obtain dose information that successfully treated such target regions, and automatically recommend or populate a field in the record specifying a target dose for the given patient before the MR image is ever analyzed by a clinician to determine the dose information. The recommended dose can be provided using the notification/recommendation module 141. Specifically, the enhanced record is created using the record review/enhancement module 140 based on information found in validated registry records (accessible from the hospital registry 310) for one or more hospitals, as well as patient data and protocol-related data from the hospital data repository 311.

Enhanced records provide a physician with more information about how a patient or patient cohort or demographic responded to a specific treatment modality. With this information available, the physician is much better informed on various aspects of the treatment, e.g., type of treatment, pharmaceuticals or devices used, specified duration of treatment and/or dosing regimen, and adjunct therapeutics (e.g., for side-effects) that may have been a contributing factor to any adverse or favorable outcomes. The enhanced record may additionally provide adverse or favorable indications during treatment that are specific or unique to the modality chosen to treat the patient and possibly of greater or lesser importance given the patient's demeanor, lifestyle, or demographic known through the physician-patient relationship. Using the enhanced record, the physician is better able to draw inferences and reach conclusions about whether the same protocol would be advisable for his or her patient, whether any modifications are needed, and whether the schedule for treatment would be suitable given the patient's age, demeanor, lifestyle, demographic, insurance resources, etc. From this information, the physician is better equipped to confirm, reject, or consider modifications to a planned or recommended protocol.

In some implementations, after the hospital registry 310 has collected validated registry records 430 for current cancer patients or recently treated patients in a sufficient number, the physician is then able to evaluate treatment options. For example, the physician may compare differences in treatment outcomes among patients having similar diagnoses and demographics, based upon varied treatment modalities. Also, for example, the physician may compare differences in treatment outcomes for patients receiving a particular treatment, based upon differences in patient diagnoses or demographics. With one, several, or preferably many such records, a physician has information to augment treatment planning. Because all the information is maintained in a structured format, the physician can quickly and efficiently select and review only information relevant to his or her patient's specific condition and characteristics, and/or planned treatment modality.

After the record review/enhancement module 140 confirms that a record is valid or contains valid information and/or enhances information contained in the records, the record is marked as validated and stored in the registries 310 and/or 313. Validated registry records 430 stored in the registries 310 and 313, when prepared on a timely basis, provide useful information to a treating physician who selects a treatment protocol for a patient. The validated registry records 430 contain structured data so that several records can be easily searched according to a variety of criteria. Thus, provided the validated registry records 430 can be updated and created in a timely manner, they can become a valuable resource for a physician. For example, information from the validated registry records 430 can be leveraged to produce more detailed or customized records that can include, in addition to the required information for a state registry, information that is specific to a treatment modality for the patient.

Validated records 430 can be provided to the notification/recommendation module 141. The notification/recommendation module 141 processes the validated records to identify treatment information across a population and trends associated with that identified treatment information. The notification/recommendation module 141 generates recommendations for a patient based on the validated record 430 associated with that patient using the identified treatment information and trends across the population. In an embodiment, the notification/recommendation module 141 accesses the inter-hospital registry 314 to obtain validated records across multiple hospitals to identify such treatment information and trends across the population.

Figure 5:
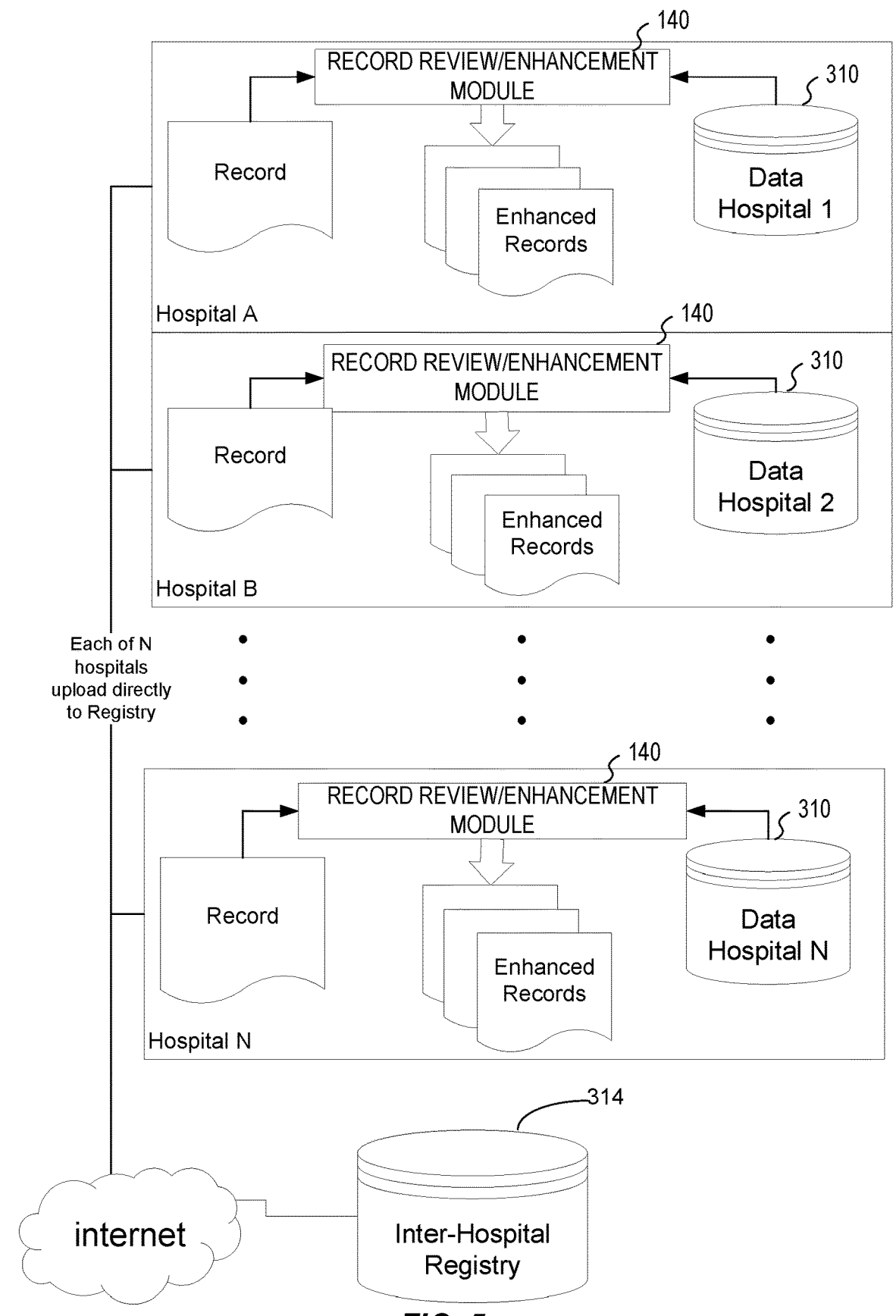
FIG. 5 illustrates an example cancer registry record-generation workflow across multiple hospitals according to some examples of the disclosure.

FIG. 5 illustrates an example cancer registry record-generation workflow across multiple hospitals according to some examples of the disclosure. The inter-hospital registry 314 is configured for providing a resource that enables one or more hospitals to obtain registry record information from other hospitals to greatly increase the number of registry records that a physician might have access to when selecting a protocol for a patient, and the number of registry records for generating automatic recommendations for treatment or notifying a physician about patient anomalies relative to a larger population. For example, by accessing the inter-hospital registry 314 a physician can derive statistical information from those records among multiple hospitals and presented through a graphical user interface. The physician can inform his or her decision making by, e.g., benchmarking a planned protocol against protocols found in the registry records based on criteria such as morbidity, quality of life, etc.

Each of N hospitals may execute a record review/enhancement module 140 locally to automatically generate records, create enhanced records, store those records in their respective hospital registry 310, and upload copies to the inter-hospital registry 314. Each of the N hospitals may then access the information stored in the inter-hospital registry 314 to interrogate the information in the inter-hospital registry 314. The inter-hospital registry 314 may be accessible to a hospital through a program run locally, e.g., on a WINDOWS or LINUX computing platform, or remotely through a web browser.

Each of the N hospitals may execute one or more versions of the record review/enhancement module 140, each with different levels of customization available for the record. For example, a basic functionality might include the registry record information provided by the record review/enhancement module 140 and additionally the functionality that allows recording and record-keeping of information for one or more types of treatment modality for the patient. An additional level of customization might include diet and health information to include in the enhanced record. Each of the N hospitals may create one or more different records that are the same as records created by the record review/enhancement module 140 executed by one or more of the other hospitals, or that differ by including more or less information about the patient, the treatment modality, etc. Thus, the inter-hospital registry 314 may include two or more registry record types that differ from one another in record content, but relate to a similar underlying condition—e.g., a specific type of diagnosed cancer.

A hospital may have access to an inter-hospital registry 314 or record types for which it does not execute the corresponding record review/enhancement module 140 and/or contribute data. Such a hospital may nonetheless use the inter-hospital registry 314 or such record types to provide treatment decision support. Based upon such access and/or use, or for other reasons, the hospital may decide to use the record review/enhancement module 140 to generate a particular registry record type of interest. It may then contribute these records of the corresponding registry type to the inter-hospital registry 314, increasing the number and potential utility of such records.

Figure 6:
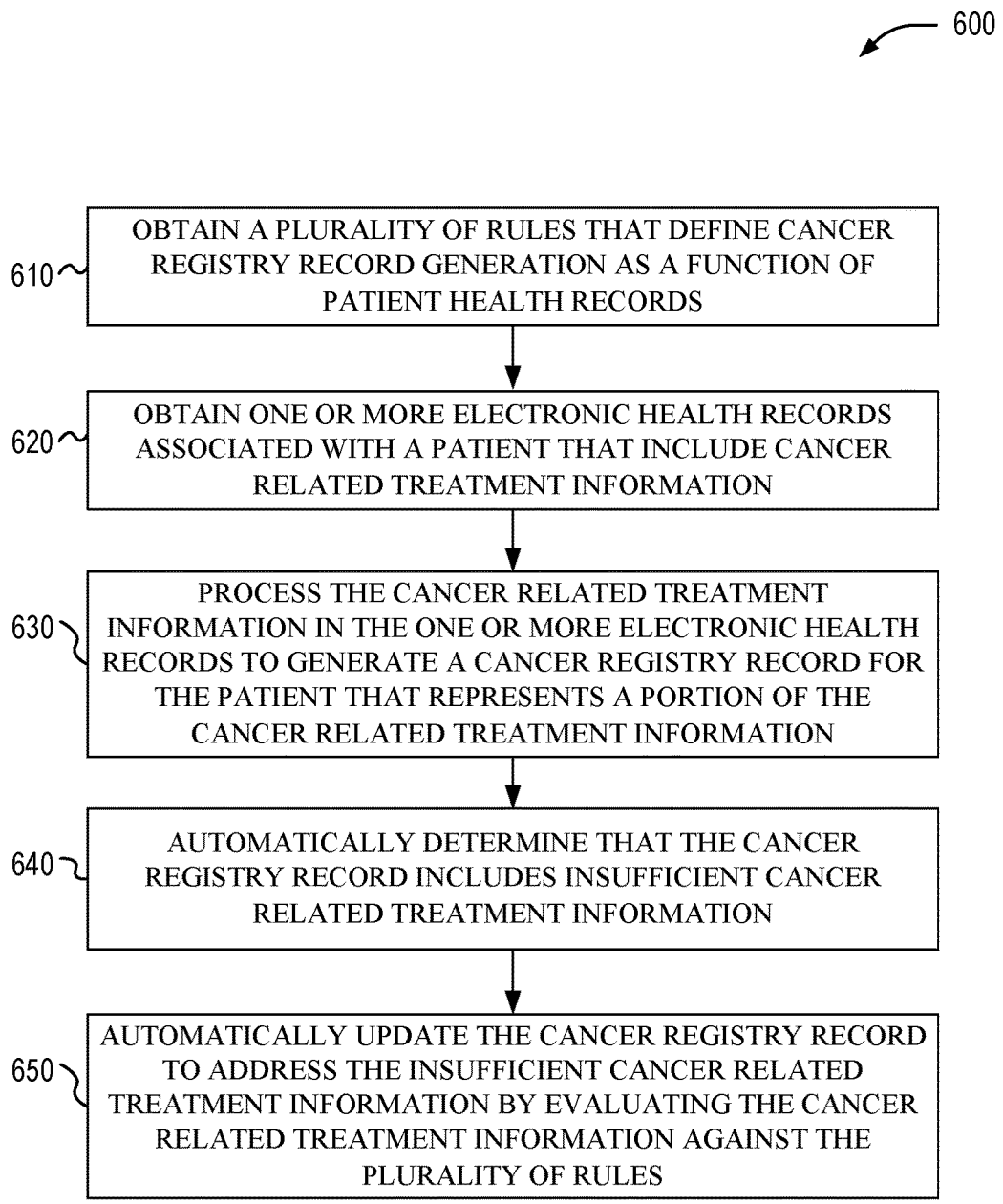
FIG. 6 illustrates a flowchart of example operations for automatically generating a cancer registry record according to some examples of the disclosure.

FIG. 6 illustrates a flowchart 600 of a process of example operations for automatically generating a cancer registry record according to some examples of the disclosure. The process can be implemented by the treatment processing logic 120 and/or any other component or combination of components discussed in connection with FIGS. 1-5. The operations of the process can be performed in parallel, sequentially, or out of order, or may be entirely skipped and omitted.

At operation 610, the treatment processing logic 120 obtains a plurality of rules that define cancer registry record generation as a function of patient health records.

At operation 620, the treatment processing logic 120 obtains one or more electronic health records associated with a patient that include cancer related treatment information.

At operation 630, the treatment processing logic 120 processes the cancer related treatment information in the one or more electronic health records to generate a cancer registry record for the patient that represents a portion of the cancer related treatment information.

At operation 640, the treatment processing logic 120 automatically determines that the cancer registry record includes insufficient cancer related treatment information.

At operation 650, the treatment processing logic 120 automatically updates the cancer registry record to address the insufficient cancer related treatment information by evaluating the cancer related treatment information against the plurality of rules.

FIG. 7 illustrates an example graphical user interface 730 of the cancer registry record-generation workflow according to some examples of the disclosure. Referring to FIG. 7, there are shown screen shots of the graphical user interface 730 generated by the treatment processing logic 120 for performing a comparison between a patient's data and population data. The user may select different data sources, categories, subcategories, and types of analysis presented in the graphical user interface 730 for running a comparison and viewing results using the user interface and the input device 148.

Depicted is a first screen 731 presenting to the user a listing of different types or categories of patient population data to choose from. After selecting the population data of interest (e.g., ID="331"), the user is next presented with a second screen 732 to review and select from a list of patients at the hospital (e.g., patient "Jane Smith"). After the patient and population are selected, the user may then be presented with a third screen 733, which presents a summary of the patient data found in a selected record 734 (e.g., categories A, B, C, and D) and a summary of categories of population data for a selected population 735 (e.g., categories 1, 2, 3, and 4). This screen may also present a "Statistics" 739 section with interactive options for selecting different statistics to run on the population data (e.g., first- and second-order statistics, and positive/negative correlations for different combinations of the categories 1, 2, 3, and 4); an interactive first comparison type option 737 for finding patients from the population data who are most similar to the selected patient, and/or more specifically for finding a similarity to one or more of the A, B, C, and D categories in the record 734; and an interactive second comparison type option 738. The graphical user interface 730 allows a given physician to view and/or generate statistics based on cancer registry records stored in one or more hospital and/or state registries.

The interactive first comparison type option 737 may instruct the device to determine what patient(s) from the population data best match the patient across all relevant types (e.g., using default criteria, choosing one or more of A-D, or listing A-D in terms of priority, e.g., ranking patients from the population best matching category A, then category B, etc.). The interactive second comparison type option 738 may instruct the device to perform different statistical analyses comparing, e.g., the patient's protocol and/or condition to the population data to determine whether there is outlier data to take into account. This analysis might, for example, present to the user certain aspects of the patient's condition or treatment plan that are common or uncommon versus the population data.

The graphical user interface 730 may present automatically generated recommendations for treatment and/or notifications about conflicts or inconsistencies generated by the notification/recommendation module 141 of the treatment processing logic 120. The physician may interact with and respond to the recommendations and/or notifications to accept a given recommended treatment or correct fields of a corresponding record in which the conflict or inconsistency is found.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiotherapy device 202, perform or implement the cancer registry record-generation workflow 130, perform or implement the operations of the flowchart 600, or perform any one or more of the other methodologies discussed herein (e.g., as part of the treatment processing logic 120 and the cancer registry record-generation workflow 130). In various embodiments, such electronic computing systems or devices operate as standalone devices or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a personal digital assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples as a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding, or carrying transitory or non-transitory instructions for execution by the machine and that cause the machine to perform any one or more of the methodologies of the present disclosure, or that is capable of storing, encoding, or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements or aspects of the disclosure or in the embodiments thereof, as is common in patent documents, to include one or more than one of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended, e.g., to mean that there may be additional elements other than the listed elements. Moreover, in the following claims, the terms "first," "second," "third," etc. are used merely as labels, and are not intended to impose numerical requirements on their objects.

The present disclosure also relates to a computing system adapted, configured, or operated for performing the operations herein. This system may be specially constructed for the required purposes, or it may comprise a general-purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include more or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including transitory or non-transitory instructions embodied thereon, such that the instructions, when executed by the processing hardware, cause the computing device to implement, perform, or coordinate the electronic operations for these techniques and system configurations and to implement modules or components described herein. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above may be provided in a distributed or centralized computing system, including any number of form factors for the computing system, such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description above.

As used herein, "module" should be taken to include a unit of distinct functionality that can provide information to, and receive information from, other modules. Accordingly, described modules may be regarded as being communicatively coupled. Modules may also initiate communication with input or output devices, and can operate on a resource (e.g., a collection of information, such as a database). Modules may include hardware circuitry, optical components, single- or multi-processor circuits, memory circuits, software program modules and objects, firmware, and combinations thereof, as appropriate for particular implementations of various embodiments. The term "module" can include an identifiable portion of code, data, or a computational object to achieve a particular function, operation, processing, or procedure. As used herein, "module" or "component" includes a software or source code file, or set of software instructions contained, or not contained, in a source code file and existing on a non-transitory or transitory memory medium. A module may exist as a standalone program or represent a program called by another program. A "component" is a portion of a "module" in the sense that the module calls a component to perform a task or tasks.

As referred to herein, "structured data" includes information characterized by a high degree of organization, such that inclusion in a relational database (or spreadsheet) is seamless and readily searchable by simple searching techniques (e.g., a boolean word search). A validated registry record has fields occupied by only structured data. "Unstructured data" as used and construed includes data that cannot be seamlessly imported or stored in a relational database or spreadsheet. A "data repository" includes a database, data warehouse, data lake, or combination of these things. As used herein, a "database" should be taken to include a centralized or distributed database and includes a SQL database. A database refers to a structured set of data that is accessible in a number of different ways.

A "data lake" includes a centralized repository that stores all structured and unstructured data in one centralized location. Every type of data may be stored in its native format with no fixed limits on account size, and without having to first structure, clean, or transform the data. Data elements in a data lake may be given a unique identifier and tagged with a set of extended metadata tags. This offers wide varieties of analytic capabilities. Data contained in a data lake, as opposed to data found in a data warehouse or a database, are stored in their native format and transformed later when a need arises to use the data or a portion of the data. This manner of storing and later using the data may be called the Extract-Load-Transform (ELT) strategy, which is similar to a "Schema on Read" technique. Conversely, a database or data warehouse may follow an Extract-Transform-Load (ETL) strategy in which the transformation of data occurs before it is stored in the database or data warehouse—this is referred to as "Schema on Write" because the schema, i.e., structure of the data, must be defined before the data is loaded to the database or data warehouse. A data lake can co-exist with a database and is accessed by accessing identifiers and metadata tags.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above detailed description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the detailed description, with each claim standing on its own as a separate embodiment.

What is claimed is:

1. A computer-implemented method for automatically generating cancer registry records, the method comprising:
   obtaining, by processor circuitry, a plurality of rules that associate medical information with respective one or more cancer registry codes to generate a cancer registry record as a function of patient health records;
   obtaining, by the processor circuitry, one or more electronic health records associated with a patient that include cancer related treatment information;
   processing, by the processor circuitry, the cancer related treatment information in the one or more electronic health records to automatically obtain a set of medical information that is associated with the one or more electronic health records of the patient;
   automatically retrieving, based on the plurality of rules, a set of cancer registry codes corresponding to the set of medical information;
   in response to automatically obtaining the set of medical information and automatically retrieving the set of cancer registry codes, automatically creating a new cancer registry record that includes the automatically retrieved set of cancer registry codes for the patient, the new cancer registry record representing a portion of the cancer related treatment information;
   determining, based on at least one of the rules, that data in a first field in the new cancer registry record is inconsistent with data in a second field in the new cancer registry record;
   accessing additional cancer related treatment information from the one or more electronic health records to verify that the data in at least one of the first or second fields is correct, the accessing comprising:

retrieving at least one of a first type of data or a second type of data from the one or more electronic health records;

determining that the first type of data or the second type of data corresponds to a first patient parameter; and adjusting the data in the first field to represent the first patient parameter or flagging the data in the first field for review in response to determining that the data in the first field indicates a second patient parameter and that the first type of data or the second type of data corresponds to the first patient parameter; and updating the data in at least one of the first or second fields based on the additional cancer related treatment information.

2. The method of claim 1, wherein the set of medical information comprises at least one of a key term, a medical condition, a medical image information, biopsy information, blood sample information, a combination of medical conditions, or geometrical tumor information, and wherein determining that the new cancer registry record includes insufficient cancer related treatment information includes automatically determining that the cancer registry record includes missing or incomplete information, the set of cancer registry codes being automatically retrieved in response to automatically obtaining the set of medical information from the one or more electronic health records associated with the patient.

3. The method of claim 1 further comprising:
matching the obtained set of medical information with codes specified in the plurality of rules to retrieve the set of cancer registry codes;
identifying a set of fields of the cancer registry record associated with the set of cancer registry codes, wherein the retrieved set of cancer registry codes are added to the cancer registry based on the identified set of fields of the new cancer registry record; and
storing the new cancer registry record in a government-regulated registry.

4. The method of claim 1, wherein processing the cancer related treatment information comprises:
performing natural language processing to generate data representing the cancer related treatment information;
identifying the set of cancer registry codes, based on the plurality of rules, that are associated with the generated data; and
populating one or more fields in the new cancer registry record based on the identified set of cancer registry codes.

5. The method of claim 1, wherein the one or more electronic health records are in a first format and the new cancer registry record is in a second format.

6. The method of claim 1 further comprising:
determining that the portion of the cancer related treatment information corresponds to a cancer related treatment or diagnosis in response to processing the cancer related treatment information;
comparing the cancer related treatment or diagnosis with a threshold representing a frequency of the cancer related treatment or diagnosis; and
generating a notification for a user to review the new cancer registry record in response to determining that the cancer related treatment or diagnosis exceeds the threshold.

7. The method of claim 1, wherein the data in the first field of the new cancer registry record of the patient indicates that the patient is a female and the data in the second field of the new cancer registry record of the patient indicates a diagnosis of prostate cancer for the patient, wherein accessing the additional cancer related treatment information comprises:
retrieving at least one of medical imaging information or blood sample information from the one or more electronic health records;
determining that the medical imaging information or blood sample information corresponds to a male patient; and
adjusting the data in the first field to indicate that the patient is a male or flagging the data in the first field for review in response to determining that the data in the first field indicates that the patient is a female and that the medical imaging information or blood sample information corresponds to a male patient.

8. The method of claim 1 further comprising:
determining that a first type of data from the cancer related treatment information corresponds to a first code of a field in the new cancer registry record;
determining that a second type of data from the cancer related treatment information corresponds to a second code of the field in the new cancer registry record;
prioritizing the second type of data over the first type of data based on the rules; and
populating the field in the cancer registry record with the second code instead of the first code based on the prioritizing.

9. The method of claim 8, wherein the first type of data represents results of a biopsy and the second type of data represents results from medical imaging, wherein a given rule of the plurality of rules specifies a condition comprising an impossibility for a given gender.

10. The method of claim 1 further comprising:
identifying a collection of cancer registry records, associated with a plurality of cancer patients, that are similar to the generated cancer registry record, the identifying comprising filtering a plurality of cancer registry records based on a combination of a gender, a tumor type, a tumor geometry, and a diagnosis of the patient;
identifying a treatment protocol indicated in the collection of cancer registry records; and
producing a recommended treatment protocol for treating the patient based on the identified treatment protocol.

11. The method of claim 1, wherein the one or more electronic health records are retrieved from a first database that manages cancer patients of a first hospital, the method further comprising:
obtaining one or more additional electronic health records from a second database that manages cancer patients of a second hospital; and
storing the new cancer registry record among a plurality of cancer registry records in an inter-hospital registry that contains data about a population of cancer patients.

12. The method of claim 1, further comprising:
determining a last modified date of the new cancer registry record;
determining that subsequently received cancer related treatment information is associated with a later date than the last modified date of the new cancer registry record;
in response to determining that the subsequently received cancer related treatment information is associated with the later date than the last modified date of the new cancer registry record, generating a code based on the subsequently received cancer related treatment information; and updating the new cancer registry record based on the generated code.

13. A system comprising:
processing circuitry comprising at least one processor; and
a storage medium comprising instructions, which when executed by the at least one processor, cause the at least one processor to perform operations comprising:
obtaining a plurality of rules that associate medical information with respective one or more cancer registry codes to generate a cancer registry record as a function of patient health records;
obtaining one or more electronic health records associated with a patient that include cancer related treatment information;
processing the cancer related treatment information in the one or more electronic health records to automatically obtain a set of medical information that is associated with the one or more electronic health records of the patient;
automatically retrieving, based on the plurality of rules, a set of cancer registry codes corresponding to the set of medical information;
in response to automatically obtaining the set of medical information and automatically retrieving the set of cancer registry codes, automatically creating a new cancer registry record that includes the automatically retrieved set of cancer registry codes for the patient the new cancer registry record representing a portion of the cancer related treatment information;
determining, based on at least one of the rules, that data in a first field in the new cancer registry record is inconsistent with data in a second field in the new cancer registry record;
accessing additional cancer related treatment information from the one or more electronic health records to verify that the data in at least one of the first or second fields is correct, the accessing comprising:
retrieving at least one of a first type of data or a second type of data from the one or more electronic health records;
determining that the first type of data or the second type of data corresponds to a first patient parameter; and
adjusting the data in the first field to represent the first patient parameter or flagging the data in the first field for review in response to determining that the data in the first field indicates a second patient parameter and that the first type of data or the second type of data corresponds to the first patient parameter; and
updating the data in at least one of the first or second fields based on the additional cancer related treatment information.

14. The system of claim 13, wherein the operations further comprise storing the new cancer registry record in a government-regulated registry.

15. The system of claim 13, wherein the operations for processing the cancer related treatment information comprise operations for:
performing natural language processing to generate data representing the cancer related treatment information;
identifying the set of cancer registry codes, based on the plurality of rules, that are associated with the generated data; and
populating one or more fields in the new cancer registry record based on the identified set of cancer registry codes.

16. The system of claim 13, wherein the one or more electronic health records are in a first format and the new cancer registry record is in a second format.

17. The system of claim 13, wherein the operations further comprise:
determining that the portion of the cancer related treatment information corresponds to a cancer related treatment or diagnosis in response to processing the cancer related treatment information;
comparing the cancer related treatment or diagnosis with a threshold representing a frequency of the cancer related treatment or diagnosis; and
generating a notification for a user to review the new cancer registry record in response to determining that the cancer related treatment or diagnosis exceeds the threshold.

18. The system of claim 13, wherein the data in the first field indicates that the patient is a female and the data in the second field indicates a diagnosis of prostate cancer, wherein the operations for accessing the additional cancer related treatment information comprise operations for:
retrieving at least one of medical imaging information or blood sample information from the one or more electronic health records;
determining that the medical imaging information or blood sample information corresponds to a male patient; and
adjusting the data in the first field to indicate that the patient is a male or flagging the data in the first field for review in response to determining that the data in the first field indicates that the patient is a female and that the medical imaging information or blood sample information corresponds to a male patient.

19. A non-transitory computer-readable medium comprising non-transitory computer-readable instructions that cause a processor to perform operations comprising:
obtaining a plurality of rules that associate medical information with respective one or more cancer registry codes to generate a cancer registry record as a function of patient health records;
obtaining one or more electronic health records associated with a patient that include cancer related treatment information;
processing the cancer related treatment information in the one or more electronic health records to automatically obtain a set of medical information that is associated with the one or more electronic health records of the patient;
automatically retrieving, based on the plurality of rules, a set of cancer registry codes corresponding to the set of medical information;
in response to automatically obtaining the set of medical information and automatically retrieving the set of cancer registry codes, automatically creating a new cancer registry record that includes the automatically retrieved set of cancer registry codes for the patient the new cancer registry record representing a portion of the cancer related treatment information;
determining, based on at least one of the rules, that data in a first field in the new cancer registry record is inconsistent with data in a second field in the new cancer registry record;
accessing additional cancer related treatment information from the one or more electronic health records to verify that the data in at least one of the first or second fields is correct, the accessing comprising:

retrieving at least one of a first type of data or a second type of data from the one or more electronic health records;

determining that the first type of data or the second type of data corresponds to a first patient parameter; and adjusting the data in the first field to represent the first patient parameter or flagging the data in the first field for review in response to determining that the data in the first field indicates a second patient parameter and that the first type of data or the second type of data corresponds to the first patient parameter; and updating the data in at least one of the first or second fields based on the additional cancer related treatment information.

20. The non-transitory computer-readable medium of claim 19, wherein the operations further comprise:

determining a last modified date of the new cancer registry record;

determining that subsequently received cancer related treatment information is associated with a later date than the last modified date of the new cancer registry record;

in response to determining that the subsequently received cancer related treatment information is associated with the later date than the last modified date of the new cancer registry record, generating a code based on the subsequently received cancer related treatment information; and updating the new cancer registry record based on the generated code.

\* \* \* \* \*